(12) United States Patent
Goldberg et al.

(10) Patent No.: US 10,115,172 B2
(45) Date of Patent: Oct. 30, 2018

(54) SELF-ADAPTIVE CARE PLAN GOAL MODULES

(75) Inventors: Neal Goldberg, Santa Rosa, CA (US); John Ryan, Boston, MA (US); Daniel Simms, Sunnyvale, CA (US)

(73) Assignee: Koninklijke Philips N.V., Eindhoven (NL)

( * ) Notice: Subject to any disclaimer, the term of this patent is extended or adjusted under 35 U.S.C. 154(b) by 2735 days.

(21) Appl. No.: 12/296,201

(22) PCT Filed: Jan. 2, 2007

(86) PCT No.: PCT/US2007/060003
§ 371 (c)(1),
(2), (4) Date: Oct. 6, 2008

(87) PCT Pub. No.: WO2007/117719
PCT Pub. Date: Oct. 18, 2007

(65) Prior Publication Data
US 2011/0161107 A1    Jun. 30, 2011

Related U.S. Application Data

(60) Provisional application No. 60/804,587, filed on Jun. 13, 2006, provisional application No. 60/744,414, filed on Apr. 7, 2006.

(51) Int. Cl.
*G06F 19/00* (2018.01)
*G06Q 50/24* (2012.01)
*G16H 50/20* (2018.01)

(52) U.S. Cl.
CPC ............ *G06Q 50/24* (2013.01); *G06F 19/00* (2013.01); *G06F 19/3418* (2013.01); *G16H 50/20* (2018.01)

(58) Field of Classification Search
CPC ............... G06F 19/345; G06F 19/3418; G06F 19/3406; G06F 19/3475; G06Q 50/24
(Continued)

(56) References Cited

U.S. PATENT DOCUMENTS 5,673,691 A * 10/1997 Abrams et al. ................ 600/300
5,722,418 A   3/1998 Bro
(Continued)

FOREIGN PATENT DOCUMENTS

EP   0917078 A1   5/1999
EP   1164531 A2  12/2001
(Continued)

OTHER PUBLICATIONS

"Frost & Sullivan Presents Philips With 2005 Technology Leadership Award", London, UK, Dec. 12, 2005
(Continued)

*Primary Examiner* — Hiep V Nguyen

(57) ABSTRACT

A goal module (78, 198, 298) includes one or more content sessions (80, 82, 200, 202, 204, 224, 300, 318) cooperatively directed toward achieving a projected health management goal. At least one feedback path (48, 86, 140, 142, 210, 234, 312, 322, 410) provides at least one input indicative of a trend in a patient progress toward achieving the projected health management goal. A care plan manager (84) dynamically configures or modifies at least one of the goal module (78, 198, 298) and content sessions (80, 82, 200, 202, 204, 224, 300, 318) based at least on the one input and intervention rules so that the patient's progress toward the projected health management goal is optimized.

28 Claims, 7 Drawing Sheets

Figure 1:
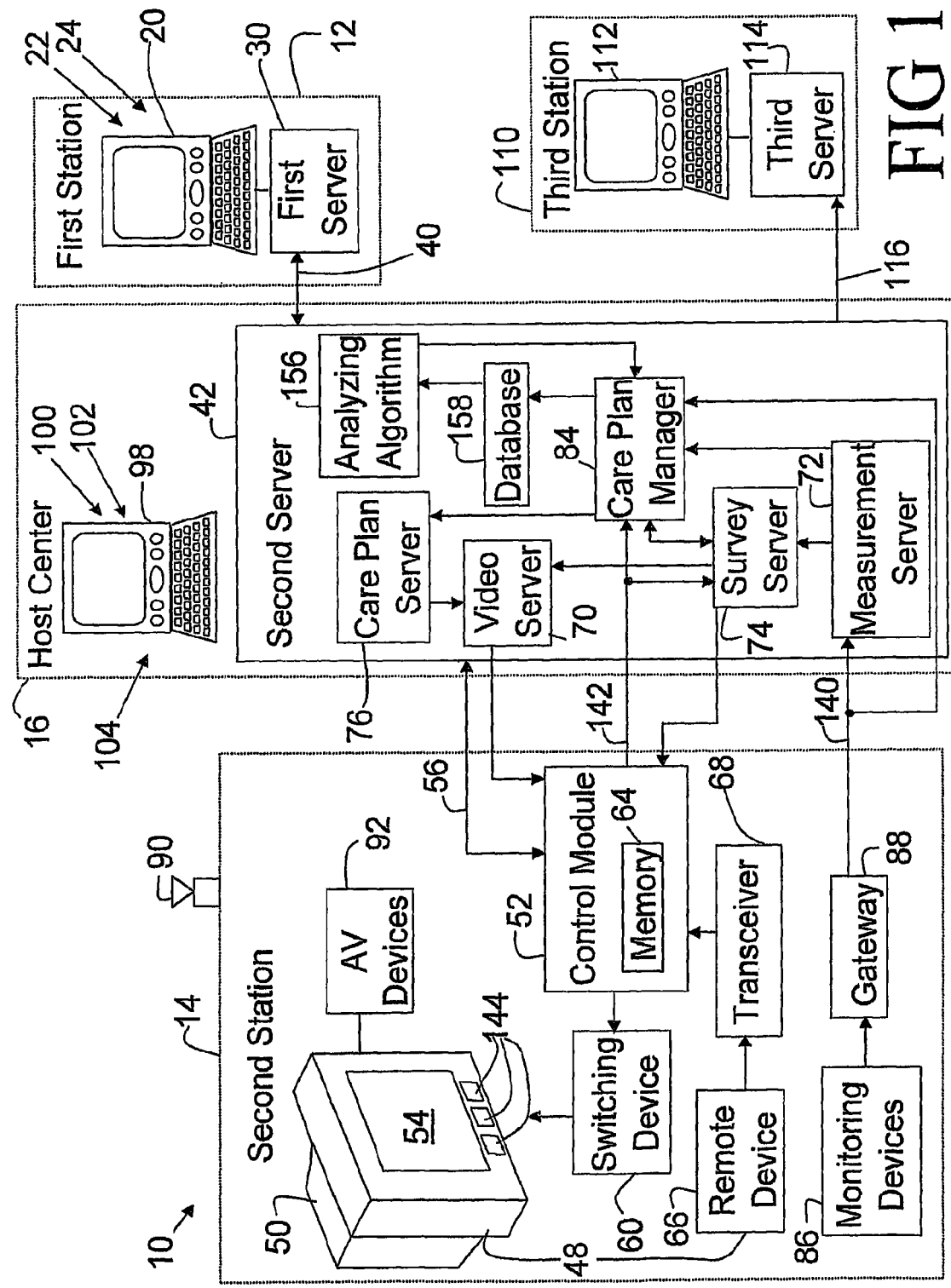

(58) Field of Classification Search
USPC .......................................................... 705/3
See application file for complete search history.

(56) References Cited

U.S. PATENT DOCUMENTS

| | | | |
|---|---|---|---|
| 6,039,688 A | | 3/2000 | Douglas et al. |
| 6,769,915 B2* | | 8/2004 | Murgia et al. ................ 434/236 |
| 2001/0012913 A1 | | 8/2001 | Iliff |
| 2001/0029340 A1 | | 10/2001 | Mault et al. |
| 2002/0055859 A1 | | 5/2002 | Goodman et al. |
| 2002/0133377 A1 | | 9/2002 | Brown |
| 2002/0183599 A1 | | 12/2002 | Castellanos |
| 2003/0009356 A1 | | 1/2003 | Hildebrand et al. |
| 2003/0022141 A1 | | 1/2003 | Packard |
| 2003/0069752 A1* | | 4/2003 | LeDain et al. .................... 705/2 |
| 2003/0125609 A1 | | 7/2003 | Becker |
| 2003/0186202 A1 | | 10/2003 | Isensberg |
| 2004/0078232 A1 | | 4/2004 | Troiani |
| 2004/0122701 A1 | | 6/2004 | Dahlin et al. |
| 2004/0260155 A1 | | 12/2004 | Ciarniello et al. |
| 2005/0113649 A1* | | 5/2005 | Bergantino ................... 600/300 |
| 2005/0137466 A1 | | 6/2005 | Somov et al. |
| 2007/0173726 A1* | | 7/2007 | Kim et al. .................... 600/483 |
| 2008/0220959 A1 | | 9/2008 | Holmes et al. |
| 2011/0161107 A1 | | 6/2011 | Goldberg et al. |

FOREIGN PATENT DOCUMENTS

| | | | |
|---|---|---|---|
| JP | 2002056099 A | 2/2002 | |
| JP | 2002183312 A | 6/2002 | |
| JP | 2002259570 A | 9/2002 | |
| JP | 2002297775 A | 10/2002 | |
| JP | 2004351184 A | 12/2004 | |
| WO | 2001039089 A1 | 5/2001 | |
| WO | 03/104939 A2 | 12/2003 | |
| WO | 2005027716 A2 | 3/2005 | |
| WO | 2007117719 A2 | 10/2007 | |

OTHER PUBLICATIONS

James Warren et al, "Supporting Special-Purpose Health Care Models Via Adaptive Interfaces to the Web", Elsevier, 2002, p. 259-265.

Hegarty, D., "Taking health personally: Making telehealthcare attractive to those who need it", Philips Research, Sep. 2005.

Finkelstein, J. et al., "Home Automated Telemanagement in Hypertension", University of Maryland School of Medicine, Baltimore, MD, 2004.

"Motiva* Interactive healthcare platform", Dec. 25, 2005, XP055216637, URL: http://web.archive.org/web/20051225070854/http://www.medical.philips.com/main/products/telemonitoring/products/motiva/index.html.

"Philips Motiva Remote Patient Management Platform", Mar. 16, 2006 (Mar. 16, 2006), pp. 1-2, XP055216634, Retrieved from the Internet: URL:http://web.archive.org/web/20060316014848/http://www.medical.philips.com/main/products/telemonitoring/assets/docs/MotivaFactsheet.pdf.

Press Information, "Philips to begin pilot study of TV-based solution to help patients manage their health from home", EPO Form 2906 01.91 TRI, Oct. 15, 2004 (Oct. 15, 2004), XP055216643, Retrieved from the Internet: URL:http://web.archive.org/web/20060311224819/http://www.medical.philips.com/main/products/telemonitoring/assets/docs/Motiva_Press_Release_FINAL.pdf.

* cited by examiner

SELF-ADAPTIVE CARE PLAN GOAL MODULES

CROSS REFERENCE TO RELATED APPLICATIONS

This application claims the benefit of U.S. provisional application Ser. No. 60/744,414 filed Apr. 7, 2006, which is incorporated herein by reference.

The present application relates to the health management arts. It finds particular application in conjunction with the patient care plan optimization and will be described with the particular reference thereto. It also finds application in conjunction with the remote patient monitoring, surveying, and the like.

The outpatient or remote health care management system typically connects chronically ill patients and health care providers via an interactive health care communication platform, which, for example, uses the patient home television set or computer terminal. Initially, a patient undergoes an enrollment process during which an initial health care plan is assigned. The initial health care plan is assigned based mainly on disease and acuity identification, non-disease risk identification and stratification and typically includes a schedule or timeline, goal modules, messages, assessments, and intervention rules. The schedule is the timeline that determines when care plan elements will be delivered to the patient or the care manager. The goal modules are care plan elements focused on patient behavior modification or education. Typically, a goal module is comprised of an ordered set of media element, such as videos, along with patient surveys and quizzes. Messages are communications sent to the patients, typically on their TV. An assessment is, for example, a group of questions that requires input regarding the patient status. For example, multiple choice surveys and quizzes are sent to determine how well the patient is doing on the care plan through certain symptoms the patient is experiencing, to define barriers to self care, and to determine if the patient understands the information provided in videos.

Typically, the patients use the medical devices, which are installed in their homes, to measure vital signs such as blood pressure, heart rate and weight. Each patient's biometric data is automatically sent via secured cable, telephone, or satellite connection links to the supervising health care providers. The health care providers monitor the patient's health by setting up the flags for clinical reviews based on feedback received from the patient, for example, if the vital sign measurements fall outside the normal range or answers to the survey include an item of interest that might require a follow up. If the assigned care plan is less than optimally effective, a clinician manually adjusts the care plan/goal modules based on the feedback from the patient, typically, via a phone or an office visit.

However, staffing shortages and labor costs make such method not only burdensome, but also ineffective due to infrequent interaction between the patient and clinician.

The present application provides new and improved methods and apparatuses which overcome the above-referenced problems and others.

In accordance with one aspect, a health management system is disclosed. A goal module includes one or more content sessions cooperatively directed toward achieving a projected health management goal. At least one feedback path provides at least one input indicative of a trend in a patient progress toward achieving the projected health management goal. A care plan manager dynamically configures or modifies at least one of the goal module and content sessions based at least on the one input and intervention rules so that the patient's progress toward the projected health management goal is optimized.

In accordance with another aspect, a health management system is disclosed. A care plan server communicates with a plurality of patients and stores at least a plurality of content sessions directed toward achieving a health management goal, and a plurality of patient profiles each corresponding to a respective patient. A care plan manager is configured to control presentation of the content sessions to each patient based on at least one feedback input from the patient and intervention rules.

In accordance with another aspect, a health management method is disclosed. At least one input indicative of a trend in a patient progress toward achieving a health management goal is electronically received. At least one of goal modules and content sessions are automatically electronically configured or modified based on the one input and intervention rules. The content sessions are displayed to the patient.

One advantage is that the patient care plan can be dynamically adjusted toward a particular health management goal.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 2:
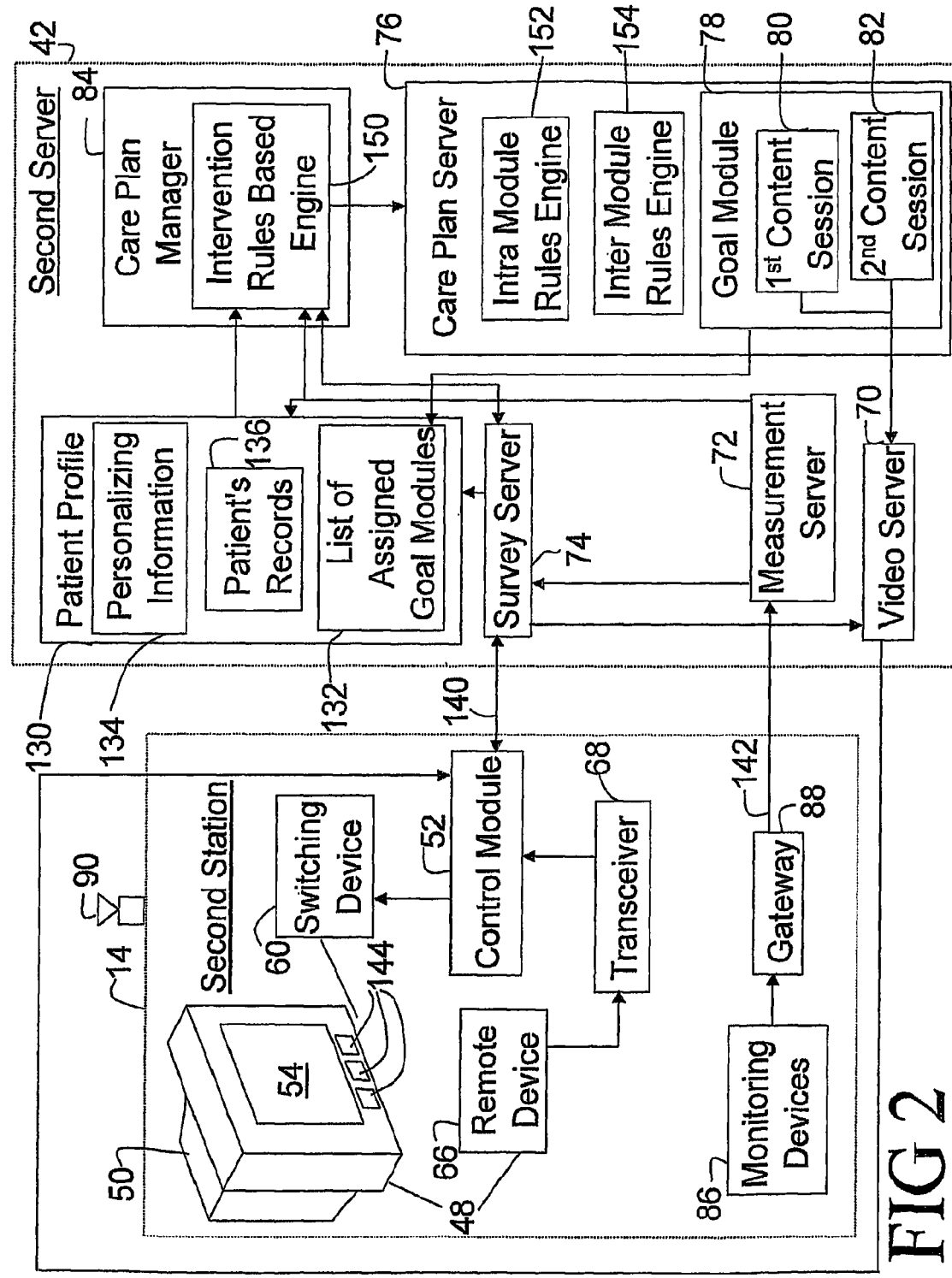
Figure 3:
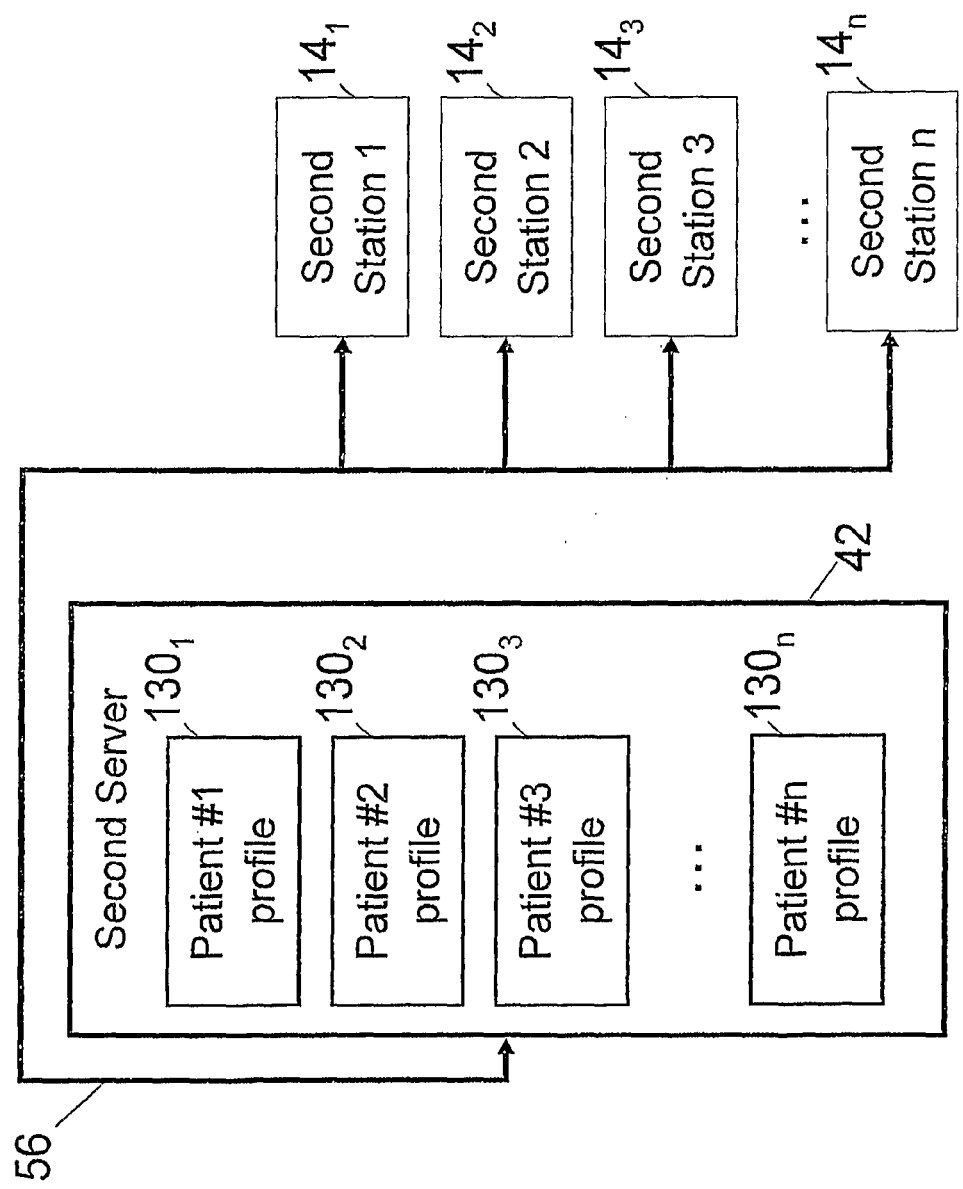
Figure 4:
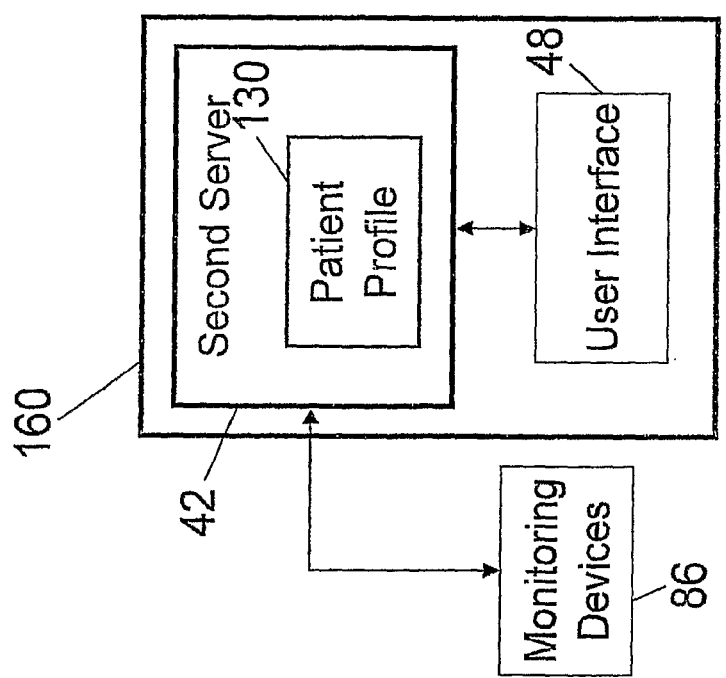
Figure 5:
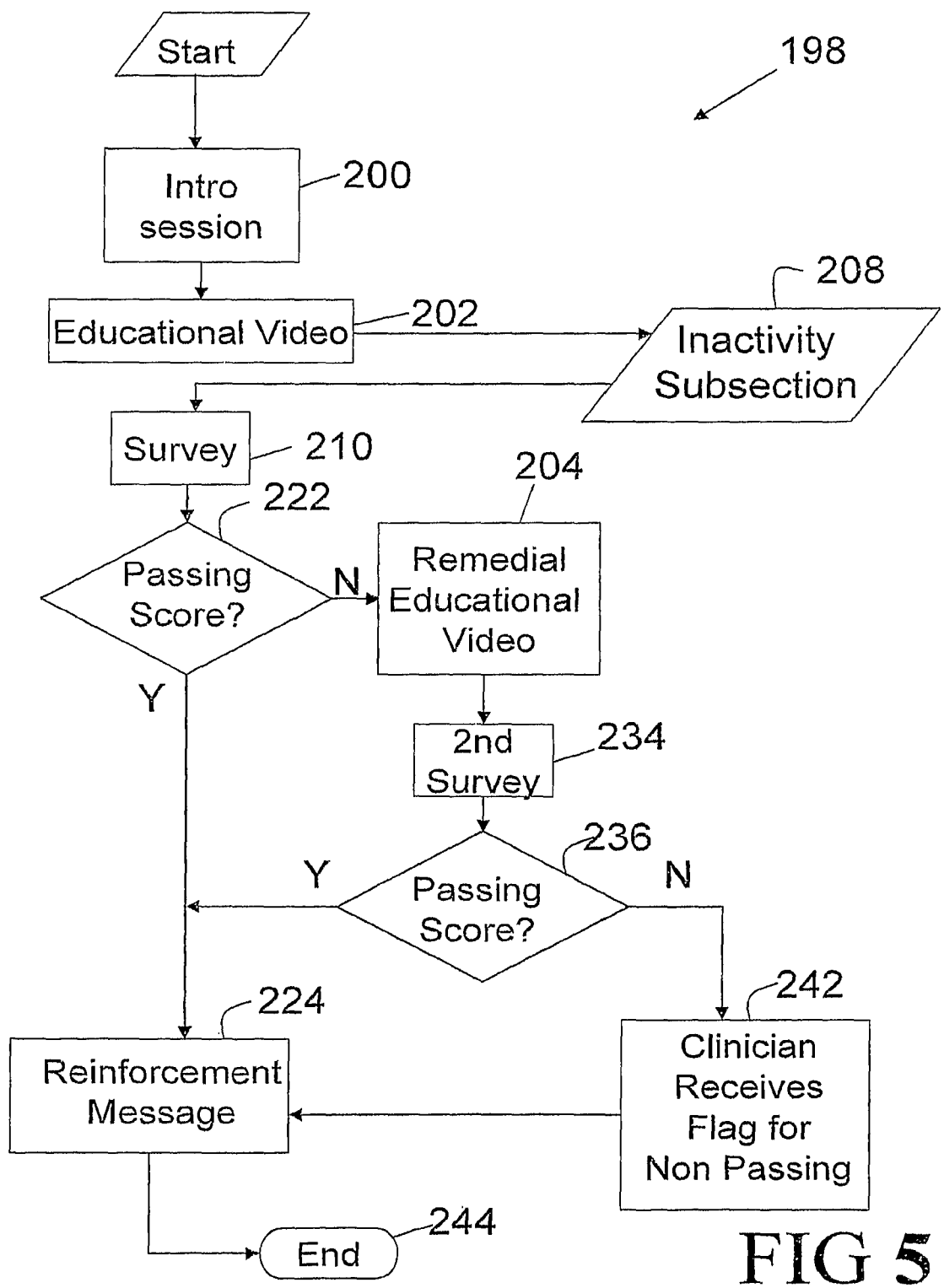
Figure 6:
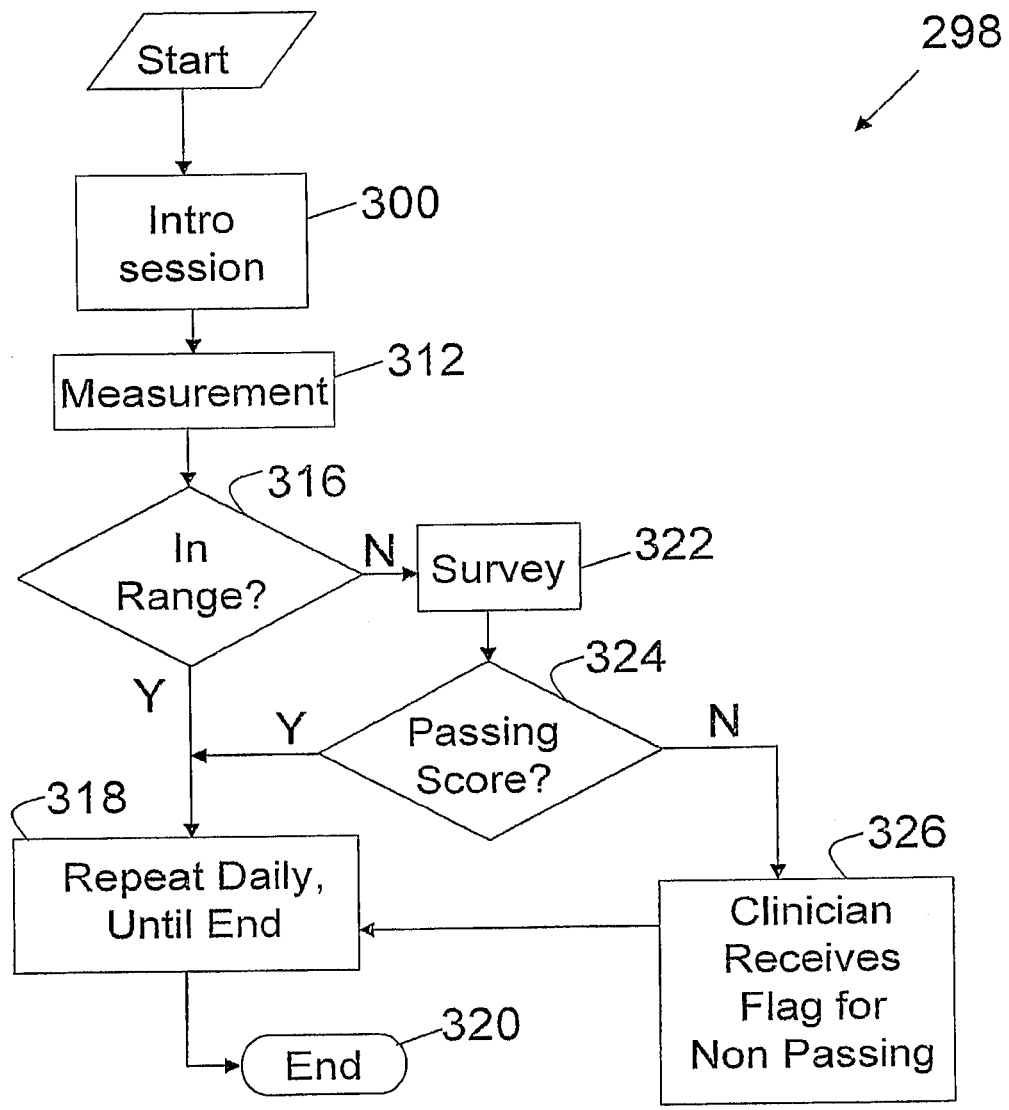
Figure 7:
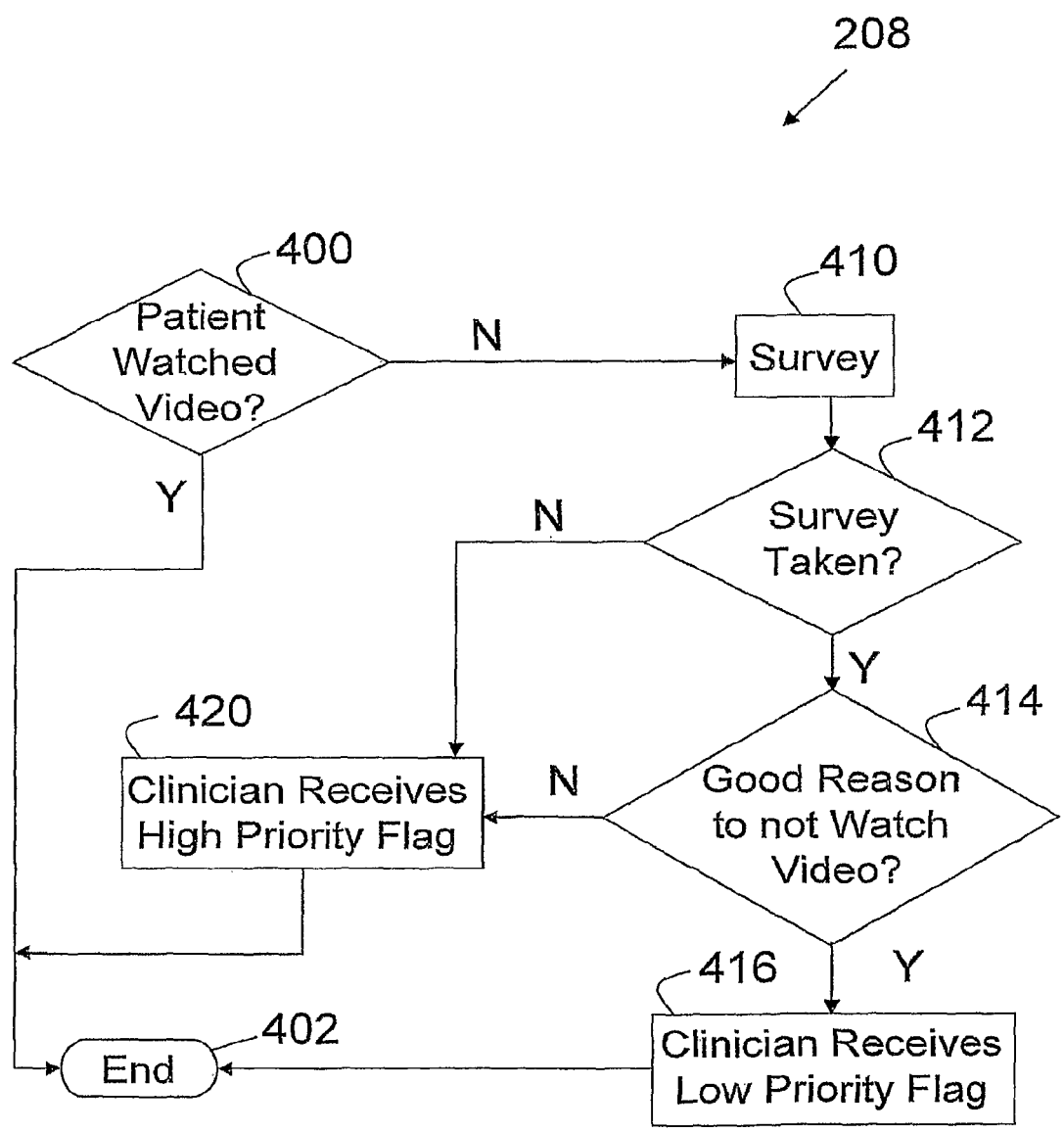

FIG. 1 diagrammatically shows principal components of an example health management system;

FIG. 2 diagrammatically shows a detailed portion of the health management system;

FIG. 3 diagrammatically shows a suitable relatively centralized arrangement of components of the health management system of FIG. 1;

FIG. 4 diagrammatically shows a suitable relatively decentralized arrangement of components of the health management system of FIG. 1;

FIG. 5 diagrammatically shows a potential educational goal module flow;

FIG. 6 diagrammatically shows content flow for an example goal module directed to the vital sign measurement; and FIG. 7 diagrammatically shows content flow for an inactivity subsection of a goal module.

With reference to FIG. 1, a health management system 10 includes first and second stations 12, 14 and a host center 16. The first or care provider station 12 is located, for example, at a care provider site such as a physician's office or hospital and includes a terminal 20. One example of the terminal 20 is a personal computer which includes appropriate software 22, such as user interface software, and hardware 24, for interfacing with the host center 16 and the second station 14. The terminal 20 is connected to a first server 30 via an intranet or other connection as known in the art.

Of course, it is contemplated that the health management system 10 can include a plurality of the first stations 12, a plurality of host centers 16 and a plurality of second stations 14 as appropriate for an application.

A first link 40 provides the connection between the first station 12 and the host center 16. Alternatively, the first station 12 is a wireless station of a wireless local area network (LAN) or wireless wide are network (WAN).

The second or patient station 14 includes a user or patient interface 48 including a television set 50 or other patient display device which is located in a patient's home or dwelling. The user interface 48 further includes a control module, processor, algorithm or other means 52, such as set-top box, which interfaces with a video display 54 of the television set 50. The control module 52 converts and displays data from analog cable, digital cable, satellite, or digital broadcast television to a standard channel frequency, e.g. channel number, for display, for example, on a standard analog television set 50. In one embodiment, the control module 52 further receives on or off-air digital or conventional analog television (DTV) signals from a cable or satellite provider or local broadcast TV for display on a DTV monitor. The control module 52 also receives signals such as digital or analog television format signals and patient information signals from the host center 16 via a second link 56. The examples of the second link 56 are wired connection, wireless connection, satellite connection, fiber optic connection, and the like.

The control module 52 is connected to the video display 54 via a switching device, algorithm or means 60 such as an audio/video (AV) switching device as known in the art. The switching device 60 provides switching between television reception from the tuner of the display 54 (or VCR, DVD or the like) and patient information reception/transmission from/to the host center 16. Alternatively, any other known type of input device adapted to provide an interface to the video display 54 is used.

For example, the patient information signals include information, instructions and queries that are displayed on the video display for information, action, and the like. The patient information signals include video and audio health issue programs, audio programs, video messages and audio messages, reminders to send health or biometric information, and the like. For example, the control module 52 can include a memory 64 so that patient information signals are stored for later use, e.g. time-shifted display. When the switching device 60 is configured to transmit the patient information signals, the control module 52 retrieves the patient information signals from the memory 64 to the display 54 or forwards the signals as received. The user interface 48 further includes a remote interface device 66 which provides signals to an infrared transceiver 68. Signals from the transceiver 68 are provided to the control module 52 and function to select video input to the video display 54, input patient information, and the like. In one embodiment, the remote interface device 66 is a remote control device such as one commonly used in the home entertainment systems. In another embodiment, the remote interface device 66 is a computer input interface device, such as a keyboard or a mouse.

With continuing reference to FIG. 1 and further reference to FIG. 2, the host center 16 is centralized and includes various servers for specific functions. The examples of servers of the host center 16 are a video server 70 which provides pertinent video content to the display 54, a measurement server 72 which receives patient's measurements, a survey server 74 which generates surveys, a care plan server 76 which includes one or more goal modules 78 each including one or more content sessions 80, 82 cooperatively directed to addressing the health issues of a specific patient, and others. It is also contemplated that the host center 16 is distributed, with different components or sub-centers hosting different functions. Alternatively, there may be a plurality of host centers 16 that connect a plurality of second stations 14 with one or more first stations 12. As described in greater detail below, a care plan manager 84 oversees and adjusts operation of the survey, measurement, and health care servers based on various criteria and rules. For example, the care plan manager 84 monitors the patient's measurements, reviews the patient's surveys, makes a judgment of the patient's progress toward the health care requirements and determines whether changes, additions, or deletions need to be made to the patient's care plan, e.g. changes, additions, or deletions to at least one of the goal modules 78 or content sessions 80, 82. Modifications to the health care plan can be done automatically by the care plan manager 84, after an approval of the clinician or planer, or automatically in some instances and by a prior approval in others based on some pre determined criteria or rules. In one embodiment, the care plan manager 84 reports to the clinician the feedback collected from the patient or observations inferred. Based on the report, the clinician makes the care plan modification. In another embodiment, the care plan manager 84 recommends a health care plan modification to the clinician. When changes are determined to be required or suggested to the clinician, the care plan manager 84 issues a notification to the clinician indicating a priority status for the change which can depend, for example, on a degree of change, urgency of change, time period since change request was entered, etc. E.g., higher priority change requests can have an elevated notification means.

With continuing reference to FIG. 1, the second station 14 includes a set of patient monitoring or biometric devices 86. The examples of the patient monitoring devices 86 include a weight scale, a blood pressure device, an electrocardiogram, an electroencephalogram, an oximeter, a brain wave measuring device, a respiration monitor, a thermometer, and the like. In a typical arrangement, the user is located at a dwelling such as a house, apartment, assisted living apartment, or so forth, and does not have ready access to medical personnel. Accordingly, in some embodiments the biometric devices 86 are advantageously designed to be simple to operate. For example, a fingertip $SpO_2$ monitor can be used to provide both saturated blood oxygen level and heart rate simply by clipping the fingertip monitor onto the patient's fingertip. The biometric devices can be wireless devices which are worn by the patient and communicate biometric reading continuously or at intervals to the host center, can be cabled devices which the patient uses one or more times a day to take readings, or the like. Additionally, or alternatively, certain measurements may be manually entered by the patient via the remote device 66. Alternatively, the biometric device 86 can be implanted in the patient, such as a sensor on a pacemaker, on an infusion pump, and the like. Collected monitored or manual patient data are provided to a measurement gateway 88, which transmits the data to the measurement server 72 for processing and use.

Other exemplary user interface devices are a personal computer (PC), personal digital assistant (PDA), a mobile phone, a portable computer, automated voice response system and the like. As such, the display is accordingly a computer monitor, handhold communication device display, such as a portable phone, cellular phone or PDA.

In one embodiment, the second station 14 includes an RF interface 90 such as an antenna and audio/video (AV) devices 92 which provide links to the second station 14. The examples of the AV devices 92 are a video cassette recorder (VCR), a digital video disc (DVD) player, a cable box, and the like.

The host center 16 includes a host center terminal 98 including appropriate hardware 100, software 102 and communications links 104 to enable connectivity between the first and second stations 12, 14.

Optionally, the health management system 10 includes an information or third station 110 which provides access to the patient information to the authorized users, such as selected family members and friends, via an access terminal 112 connected to a third server 114. The examples of the access terminal 112 are a personal computer, a video display including a control module, a PDA, a portable computer, a cellular telephone, and the like. The connection of the third station 110 to the host center 16 may be a third link 116 wired or wireless connection.

With continuing reference to FIG. 1 and reference again to FIG. 2, typically, the patient is initially assessed and assigned an initial care plan upon enrolling into the health management system 10. Thereafter, the care plan manager 84 evaluates the patient's progress toward an assessed goal based on patient feedback and adjusts the assigned care plan by changing the interactions and content delivered to the patient. The adjustment of the care plan can be done on on-going basis, dynamically, continually, periodically, on request, and the like. More specifically, the care plan is organized into the goal modules 78. An example goal module 78 includes the content sessions 80, 82. However, it is to be appreciated that typically the care plan server 76 includes a number of goal modules 78, each directed toward a particular health management goal. For example, different goal modules may be provided based on a patient need or a prescribed need by the clinician that are directed toward: reducing weight; stopping smoking; learning to self-administer a medical intervention such as a medication, a biometric monitor, or so forth; learning to follow a dietary restriction such as a low-salt diet; learning to follow a dietary requirement such as a high-fiber diet; performing a physical exercise; or so forth. Moreover, a typical goal module 78 may include more than the illustrated two content sessions. The number of content sessions in a given goal module 78 can vary between one content session for a very simple goal module, to five, ten, or more content sessions for a complex goal module. The content sessions can include various types of content, such as: pre-recorded audio/video content; textual content; interactive survey, quiz, questionnaire, or test content; pre-recorded step-by-step interactive audio/video content; and so forth.

The care plan manager 84 delivers content related to specific health management goals that a given patient or other user is or should be striving to achieve in his or her personal health management program. To enable personalized delivery of content, each patient has an associated patient profile 130 stored on the second server 42. (The term "patient" as used herein encompasses patients recovering from surgery, stroke, heart failure, or another condition, patients suffering a chronic illness that is being treated on an out-patient basis, or so forth. The term "patient" also encompasses other users of the health management system 10 who may be generally healthy but who are following a health management program assisted by the system 10 to maintain fitness, control weight, avoid osteoporosis, or otherwise maintain a healthy condition or make health-related lifestyle modifications).

The illustrated example patient profile 130 includes a list of assigned goal modules or a care plan 132 which includes the goal module(s) 78. In some embodiments, the patient can only access those goal modules assigned to the patient. The patient profile 130 may optionally include other information such as personalizing information 134 that may include name, address, diagnosis, and so forth. In some embodiments, the personalizing information 134 is used to personalize content sessions. For example, a text-based content session may include name tag placeholders that are replaced by the personal name stored in the personalizing information 134 of the patient profile 130. Optionally, the inputs provided by a patient via the user interface 48 or by the biometric devices 86 operatively connected with the patient are stored in a patient records portion 136 of the patient profile 130.

In the exemplary system 10 of FIG. 1, feedback paths include a first feedback path 140, including the user interface 48 that enables the user to provide responsive input to the survey server 74. Feedback provided by the user interface 48 may include answers to questions posed by the content, or answers to surveys, quizzes, tests, questionnaires, or the like. The feedback paths also include a second feedback path 142 including one or more monitoring devices 86 that monitor biometric parameters of the patient. By monitoring the patient biometric data and by reviewing the patient's health surveys, the care plan manager 84 makes a judgment of the patient's progress care requirements and determines whether changes, additions, or deletions need to be made to the patient's care plan. For example, the goal module for stop-smoking may include a weight monitor. If the patient starts showing a weight gain, the goal module can be modified to include weight management content such as exercise, diet, etc. If the weight gain continues to be an issue, the goal module can be modified to add a more vigorous content and/or send a notification to the clinician to determine whether further modification is needed, e.g., medication, office visit, etc. In this manner, the patient's health goal is reevaluated and the patient's progress toward the goal is optimized.

For example, if the user provides a set of responses to a survey via the user interface 48, the care plan manager 84 may grade the responses and generate a score indicating how well the patient scored on the survey. The score is then used to control content flow, for example by showing a remedial video if the patient scored low indicating lack of comprehension.

Further, the care plan manager 84 modifies the care plan 132 based on the patient profile 130 and an intervention rules algorithm, engine, or other means 150 that is configured to control the content sessions 80, 82 of the goal modules 78 based on intervention rules and the input received at least via one of the feedback paths 48, 86, 140, 142. For example, the intervention rules engine 150 is configured to control the content sessions 80, 82 of the goal modules 78 based on parameters that can be set to trigger specific actions based on specific limits. Such limits are determined in advance when enrolling the patient into the health management system 10 and/or by a specific facility's clinical rules. One example is a weight intervention rule which sends a survey if a patient is two pounds over the set baseline weight, sets a flag for a clinician to follow up, and/or sends a reminder message to the patient. As another example, the patient's vital signs are automatically compared to baseline values that were established for this patient upon enrolling. If the result indicates that the patient should take some type of action about the measurement, the intervention rules engine 150 modifies accordingly patient's care plan. Intra-module rules engine 152 associated with each goal module 78 suitably governs the flow of presentation from content session to content session within the goal module 78. Optionally, inter-module rules engine 154 governs the flow of presentation from one goal module to another goal module. For example, if the illustrated goal module provides instruction for self-administering a medication that typically causes weight gain, the inter-module rules associated with the goal module optionally call for the content flow engine to present a weight control goal module substantially concurrently with or after presentation of the goal module. (Substantially concurrent presentation can be achieved, for example, by interleaving presentation of content sessions of the two different goal modules.) Optionally, patient-specific flow rules associated with the patient profile govern content flow. For example, if the patient is a non-smoker, then the patient-specific flow rules may call for omitting presentation of any sessions related to quitting smoking. Patient-specific flow rules can substitute for rules associated with the goal module, or can supplement the goal module rules.

For example, at a prespecified time intervals, the survey server 74 generates health surveys. The survey server 74 generates surveys based on objective or subjective data, such as how one feels, abnormal vital signs, clinically significant data, or a prior completed (or not completed in time) survey. The user interface 48 enables the patient to input answers to the survey. The survey answers represent a portion of the first feedback path 140 via which the survey answers are forwarded to the survey server 74.

In one embodiment, the survey server 74 generates a reflexive survey based on one or more triggering events in the monitored vital signs measurement data which is included in the second feedback path 142 and forwarded to the measurement server 72. The measurement values are forwarded to the survey server 74. For example, for a patient having an abnormal heart rate, the survey server 74 generates a reflexive survey designed to query the patient about his heart or other conditions such as a change in a lifestyle that might have affected the heart. The survey server 74 customizes the reflexive survey on a dynamic basis and/or uses previously developed questions and answers accordingly to the triggering event which generates the item of interest. For example, a received abnormal response to the survey is compared to a predetermined reflexive survey. The item of interest varies between applications and patients, however, the item of interest covers any aspect of the patient that is deemed interesting, including any abnormal or medically significant data, patient diagnosis information, patient mental or physical state.

In one embodiment, the survey includes a list of questions, possible answers from which the patient can select, and path information to navigate the question list. The survey questions probe into why a patient's weight, blood pressure, pulse rate and/or other measurements may be abnormal or unexpected, and provide the clinical user with additional information about the patient's condition. The surveys are initiated by rules applied to patient physiological measurements and patient responses to subjective questions.

In one embodiment, the survey is sent to the third party. This can be helpful as the third party, e.g. a family member, a care giver, etc., may be in a better position to notice changes in the patient, such as depression, which might be contributing to the identified abnormal condition of the patient.

The surveys can be performed intermittently or routinely. For example, check up surveys might be delivered several times a week, while more comprehensive assessments might be performed every three or six months. Health surveys help to determine symptoms a patient may be experiencing, define barriers to self care, determine whether or not the patient is in compliance with the prescribed health regimen, or whether or not the patient understands the information provided in the videos.

In one embodiment, maintenance of the care plan server 76 is performed by an administrator, for example, via the host center terminal 98. The administrator may, for example, add goal module and/or content sessions, delete obsolete goal modules and/or content sessions, modify or update goal modules and/or content sessions, modify or update content flow or intervention rules, configure the patient profile format, and so forth. The patient profile 130 is suitably maintained in accordance with a diagnosis or other information provided by the patient's doctor or other medical personnel. In some embodiments, medical personnel such as doctors or nurses can generate and/or update the patient profile 130 by directly accessing the second server 42 via the first station terminal 20. In other embodiments, one or more system administrators perform all creation and updating of the patient profile 130 via the host station terminal 98, and in accordance with instructions from the patient's physician or other medical personnel.

As described above, the user interface 48 can employ substantially any hardware capable of providing content presentation in unmodified and/or augmented form and capable of providing feedback to the second server 42. For example, the user interface 48 can be embodied by hardware such as: a desktop computer; a laptop computer; a personal data assistant (PDA); a cellular telephone (i.e., cellphone); a television set having Internet connectivity integrally included and operated by a television remote control or other input device; a digital or analog television set having Internet connectivity provided by an add-on set-top unit and operated by a television remote control, set-top unit remote control, or other input device; or so forth. The components of the second server 42 can be embodied in various ways, such as by a centralized computer or computer server, a desktop computer, or so forth. In some embodiments, existing educational content presentation hardware, such as an analog or digital television set, is modified or augmented by a set-top box that enables the television set to be used as a user interface for accessing the Internet or another digital network.

In the manner described above, based on the review of the patient's progress toward the goal, the care plan of the patient is adjusted automatically. The automatic modification of the care plan can be responsive to any information to which the system has access such as the monitored physiological conditions, survey answers, and the like. Moreover, the system described above is responsive to a lack of change or to progress in addressing a physiological condition, such as an overweight patient, steadily reducing his weight. The system can also respond to mile posts along a self improvement program, such as reducing blood pressure 5 points, losing 10 pounds, or the like. The care plan manager automatically sends out encouraging or reinforcing information to encourage the patient to continue his current course of self improvement. As a result, fewer trips to the hospitals and fewer hospitalizations are required because triggering events are detected earlier in the chain of events and the care plan accordingly is adjusted.

The possible input types, based on which the modifications to the current health plan are contemplated, are defined by the capabilities of the overall system and include but are not limited to:
  vital sign or other (e.g. weight, blood pressure, pedometer) measurements,
  questionnaires answered by patient,
  activity (or lack thereof) on system by the patient,
  assessments made by the clinicians,
  parameters (e.g. target weight, weight loss rate, blood pressure, exercise) set by the clinicians Similarly, the possible output types of the care plan and goal modules are limited only by the capabilities of the overall system and include but are not limited to:

schedule vital sign or other measurement to be taken
schedule questionnaire to be answered
schedule video to be watched
change a schedule of videos to be watched
send message to the patient
increase/decrease a frequency of reinforcement feedback
customize reinforcement messages
schedule assessment to be made by the clinician
notify the clinician or administrator Therefore, a care plan is adaptive as defined by the care plan designer via a set of predetermined rules. Similarly, the whole set of care plans is adaptive through the stratification step (i.e. the selection of the small scale adaptive care plan). Furthermore, trends observed by the care plan designer about outcomes, utilization, activity and other proxy measurements may be used to reprogram care plans, so the system is large scale adaptive (i.e. at a higher level and longer time-periods) through the designer.

In one embodiment, the response of the patient to various stimuli, e.g. vital sign measurement, assessment, survey, is treated as a dynamical system. Although non-linear models are also contemplated, a linear model is explained in the following for simplicity of understanding. One form of the dynamic system equation is to find several constrained, linear approximations to the response-stimuli model and treat the choosing of content as a constrained optimization problem:

$$\text{prediction}(t+1) = \text{state\_history}(t)\ \text{state}(t) + \text{stimuli\_response}(t)\ \text{stimuli}(t)$$

where the constraints are:
the elements of stimuli(t) should, in this example, either be 1 or 0, indicating the particular content or interaction is delivered at time t
the desired state, possibly including smoothness or other qualities of the state change through the usual replication in the state vector, is known Such model can be used to predict the given program of stimuli (i.e. interactions or content) for any specific patient or adapt to changes as the predicted state differs from the measured state. Furthermore, selection of the linearized model can be identical or coincidental with the non-linear stratification step, so the system is also medium-scale adaptive.

In a preferred embodiment, an analyzing algorithm, processor, device or other means 156 analyzes the patient response to the stimuli and updates the variables, e.g., stimuli_response, in a database 158 through the analysis of not only individual results, but also of system results on a population basis. E.g., the probability that the response to stimuli will invoke this particular response for this particular population segment is updated based on comparing the response to historical "experiments." The intervention rules engine 150 updates the intervention rules and the care plan manager 84 selects the highest probability stimuli to be applied to the dynamic adjustment of the content sessions.

With continuing reference to FIG. 2 and further reference to FIG. 3, in a relatively centralized example arrangement of components of the health management system 10, the second server 42 which includes at least corresponding video server 70, measurement server 72, survey server 74 and care plan server 76, is a centralized server that services in the manner described above a plurality of patients at second station locations $14_1, 14_2, 14_3, \ldots, 14_n$. Each patient has a corresponding personalized patient profile $130_1, 130_2, 130_3, \ldots, 130_n$. Communication between the patients and the remote centralized second server 42 is achieved by a wired or wireless network connection 56. For example, the network connection 56 can be a secure high-speed wireless or wired Internet link. The network connection 56 is advantageously a secure link because private medical information may be conveyed across the network connection 56. However, unsecured connections can also be used. In some embodiments, a patient may have more than one user interface. For example, if the second server 42 is accessible by a high-speed Internet connection, then the user may be able to access the second server 42 via the patient's home computer, personal data assistant (PDA), Internet-enabled cellular telephone, television set having Internet connectivity integrally included and operated by a television remote control, television set having Internet connectivity provided by an add-on set-top unit and operated by a television remote control, or other Internet-capable device. If the second server 42 is accessible by a cable television network, cellular telephone network, or so forth, then the user may be able to access the second server 42 by a respective cable television set, cellular telephone (i.e., cellphone), or so forth.

With continuing reference to FIG. 2 and further reference to FIG. 4, in a relatively decentralized example arrangement of components of the health management system 10, the second server 42, which includes at least corresponding video server 70, measurement server 72, survey server 74, and care plan server 76, and the user interface 48 are embodied by a patient computer 160, personal data assistant (PDA), or other digital electronic device disposed at the dwelling of the patient or carried with the patient or otherwise readily accessed by the patient. The personalized educational content can be downloaded from the first station terminal 20 via a cable or satellite television network, cellular telephone network, the Internet, or otherwise loaded onto the patient computer 160, smart television, PDA, cellphone, or other device. Optionally, the host center terminal 98 may also include, for example, a secure Internet connection between a hospital computer and the patient computer 160 by which patient responses or biometric data are communicated to the doctor or hospital on a daily, weekly, or other time basis. Because in the embodiment of FIG. 3 an entire personalized instance of the health management system 10 is provided to the patient, there is typically only a single patient profile 130 corresponding to the single patient at that dwelling. It will be appreciated, however, that in the decentralized arrangement of FIG. 4, each patient will have his or her own personalized instance of the health management system 10 which will include that patient's personalized personal profile.

The centralized and decentralized arrangements or layouts of components of the health management system 10 depicted in FIGS. 3 and 4 are illustrative examples. Other arrangements can be used. For example, in some embodiments certain portions of the second server 42 may reside at a centralized server computer while certain other portions of the second server 42 may reside at the patient's computer. For example, the server may be located on a centralized server computer at the hospital or other centralized location and store the content sessions and patient profiles for a number of patients, but the intervention rules engine 150 may be an executable program downloaded to and executing on the patient's computer located at the patient's dwelling. In some embodiments, duplicate copies of portions of the second server 42 or portions thereof may reside at both a centralized server computer and the patient's computer. As an example of this latter arrangement, the patient's biometric measurements may be stored at the patient's computer for ready access by the patient, and also transmitted to a centralized server computer for review by the doctor.

With reference to FIG. 5, the content flow of a typical educational goal module 198 presentation is described. The illustrated goal module 198 includes four content sessions 200, 202, 204, 224. The first content session 200 is an introductory session. The second content session 202 provides an educational video for the patient to watch. The third content session 204 is a remedial educational session. The introductory content session 200 is presented first, and may for example present text and optional graphics or video that introduce the goal module to the patient and give the patient a preview of what is covered by the goal module. The educational video 202 is presented next. The educational video 202 may, for example, provide step-by-step interactive instruction on using a piece of equipment. After presentation, if in an inactivity subsection 208, which is described in detail below, it is inferred that the user watched the prescribed video, the user is presented with a survey 210. The survey 210 may, for example, include questions about the material presented during the session 202. If the answers were affirmative, then at a decision point 222 based on a score, it may be inferred that the user has successfully learned how to use the equipment, and so the patient is next presented a reinforcement message 224 which may include a congratulatory or encouraging text or video message. On the other hand, if the patient did not achieve the score, then at the decision point 222 it may be inferred that the user was unsuccessful in learning how to use the equipment, and so the user is presented with a remedial educational video 204.

If presented, the remedial session 204 repeats the equipment training in a slower, more detailed manner. The transition to the remedial session 204 is optionally transparent to the patient, who may perceive the remedial equipment training session 204 as a continuation of the first session 202. Such a transparent transition may be useful if the patient is likely to become discouraged if told he or she requires remedial training.

After the presentation, the user is presented with a second survey 234. The second survey 234 may, for example, be a questionnaire, the score of which indicates how well the patient comprehended the instruction. If the patient gets a high enough score, then at a decision point 236 it is inferred that the user has successfully achieved the educational goal of the educational goal module, and so the user receives the reinforcement message 224, which may include a congratulatory or encouraging text or video message. On the other hand, if the patient's score is too low, then at the decision point 236 it may be inferred that the user has not yet achieved the educational goal, and so a clinician receives 242 a flag for non passing. Content flow terminates at an end 244.

With reference to FIG. 6, an example content flow for a vital sign measurement goal module 298 is illustrated. A first content session provides an introductory video 300, which introduces the topic to the patient and identifies the goal to be achieved, for example to measure blood pressure. The introductory content session 300 is immediately followed by an actual measurement 312 provided by the biometric devices 86.

Based on the biometric measurement 312, a decision 316 is made based on whether the measurement is in an appropriate range. If so, then a reminder 318 is presented that reminds the patient to repeat the vital measurement session daily. The module terminates at 320. On the other hand, if at the decision point 316 it is inferred that the measurement is not in the range, then the patient is presented a survey which might include questions directed to identification of the reasons that might have led to the out of range measurement. At a decision point 324, if the patient attained a passing score, the reminder content session 318 is presented. If at the decision point 324 the patient did not attain a passing score, a clinician receives 326 a flag for non passing.

With reference to FIG. 7, the inactivity subsection 208 of the goal module 198 is illustrated. If at a decision point 400 it is inferred that the patient watched the video, the inactivity subsection terminates 402. If at the decision point 400 it is inferred that the patient did not watch the video, the patient is presented with a survey 410. If at the decision point 412 it is inferred that the survey was taken, and at a decision point 414 it is inferred that the patient had a good reason to not watch the video, a clinician receives a low priority flag 416 and the inactivity subsection of the goal module is terminated 402. If at the decision step 412 it is inferred that the survey was not taken, the clinician receives a high priority flag 420. The inactivity subsection of the goal module is terminated 402. If at the decision point 414 it is inferred that the patient did not have a good reason to not watch the video, the clinician also receives the high priority flag 420.

An advantage of employing goal modules by the care plan manager is that the modules can be mixed and matched based on the goals of the patient. Using a care plan with a goal module-based approach, each goal module can be targeted narrowly toward achieving a specific narrow health goal. Goal modules simplify maintenance of the health management system.

Another aspect of the present invention that is incorporated into some embodiments is the incorporation of behavioral models into one or more of the goal modules 78 or content sessions 80, 82. Using behavioral models will allow for the assessment of patients based on their current performance against an ideal behavior and a perceived ability to achieve the ideal behavior. In this regard, subjective analysis of a patient's progress can be viewed more objectively in relation to where the patient is in terms of the behavioral model.

In some embodiments, the behavioral model is based on an ability to achieve the goal, wherein the ability is defined as a product of the patient's knowledge of the proper health behavior (K), the patient's motivation to achieve the goal (M), and the patient's confidence that the goal can be achieved (C). This can be defined as the patient's KMC. For each individual health goal, the patient's assessment of current status and KMC to achieve the ideal health state will map the patient into a position within a behavioral change continuum. There are multiple behavioral change models that can be employed. As merely one example, the Trans Theoretical Model of Behavior Change (TTM) developed by Prochaska and DeClemente can be used. In the TTM model, at least five stages are delineated, including pre-contemplation, contemplation, preparation, action and maintenance. Other stages, such as, for example, regression, uncertainty, or abandonment, can also be added to the TTM model, or different models having different numbers of stages can be used.

The stages of the behavioral model can be defined by one or more content sessions within a specified goal module 78. In some embodiments or in certain care plans, the behavioral models can be cross-goal module, in that the stages of the behavior model are defined by one or more content sessions 80, 82 in each of a set of goal modules 78. Further, in some embodiments, a number of the goal modules 78 have a corresponding behavioral model including behavioral stages, while the overall care plan has an overall behavioral model and corresponding behavioral stages.

As the patient moves through the various content sessions 80, 82 of a goal module, a set of criteria can be used to determine how the activity tracks against the behavioral model. There are numerous factors that can be used to determine the stage of the behavioral model, including, but not limited to, completion of content sessions, time taken to complete one or more content sessions, the time between access of the care plan, feedback or answers from questions posed directly by a caregiver in conversation, quizzes or surveys within the content sessions, medical monitoring data taken during the content sessions, the corresponding factors in other goal modules, feedback from care providers, and feedback from body sensors. Based on these factors the behavioral model determines a stage within a specific goal module and/or a stage within the overall care plan. For example, the feedback, once processed through the TTM behavioral model, may indicate that a patient is in the contemplation stage of a first goal module and the preparation stage of a second goal module. If an overall care plan behavioral model is also used, the stage may be determined to be contemplation. As more content sessions are completed and/or other criteria change, the stage of the behavioral model for each goal module and for the care plan will also change.

In using the behavioral model described above, the care plan provider can adapt the care plan to help the patient achieve the desired health status. The manner in which the care plan can be modified includes the methods described above. Furthermore, a care provider can easily determine the patient's progress in each of the goal modules or within the care plan as a whole. While the system can also track the progress of the patient through the various content sessions, such as content sessions 1, 2 and 3 completed and content sessions 4, 5, 6, and 7 remain (or all 7 sessions (aka: Goal Modules) can be running simultaneously), such reporting system may not provide a general enough status update to allow for a quick assessment from a care provider that is not intimately involved in the care plan design, and thus does not necessarily understand the significance of the completed content sessions. Further, as described above, it may be desirable to include more factors, other than the completion of content sessions, into the stage assessment. For example, if a patient completes a certain number of content sessions, but takes five times longer than anticipated to complete the sessions, such action can show a lack of knowledge, motivation and/or confidence. Consequently, that patient may be determined to be in a different stage than a patient that completes the same number of content sessions closer to the anticipated time allotment. Another example of measuring patient performance/status would be to score their results numerically within each stage of each goal module, enabling a finer grained understanding of patient status. Use of behavioral models will allow for unified stage indicators, thereby allowing for easy review and interpretation by care providers.

Results for patient will be tracked at a very precise and detailed level, enabling measurement of absolute change from program start at the level of Goal Module (to understand content effectiveness), patient (to understand behavioral status and next steps), nurse (to understand coaching skills), sub-population (to understand care plan design effectiveness), and population (to understand overall program effectiveness). As the care providers learns what techniques/content are effective and which are not, they can utilize the capabilities to redesign and redeploy the interventions to patients, in order to continuously improve outcomes.

As a further elaboration of the concept presented above, the system may conduct an automated assessment of the patient over the Patient User Interface. If, based on the patient's inputs, the system calculates that a new care plan is required (eg: the patient now has a new diagnosis of diabetes, along with the heart failure diagnosis they had previously), the entire care plan could be self-adaptive by switching to one which manages both conditions.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A health management system comprising:
    a goal module, including a plurality of audio/visual content sessions cooperatively directed toward achieving a projected health management goal of a user;
    at least one feedback path providing inputs indicative of user progress toward achieving the projected health management goal, the feedback path including:
    a biometric device which inputs physiological parameter measurement acquired by the biometric device, and
    a survey, quiz, test, or questionnaire including at least one question presented by a user interface to test the user's comprehension of one or more preceding audio/visual content sessions, the inputs including user responses via the user interface; and
    a care plan manager, which dynamically configures, modifies, or reorders the audio/visual content sessions based on the physiological parameter measurements input by the biometric device, the user's comprehension of the audio/visual content sessions input by the user interface, and intervention rules so that the user progress toward the projected health management goal is optimized.

2. The health management system as set forth in claim 1, further including:
    an analyzing algorithm which analyzes trends of the user in response to the reconfiguration or modification of the audio/visual content sessions and wherein, based on the analysis, the care plan manager at least one of changes an order of the audio/visual content sessions and adds one or more audio/visual content sessions directed toward the health management goal.

3. The health management system as set forth in claim 1, wherein the audio/visual sessions include motivational and educational video presentations personalized to the user.

4. The health management system as set forth in claim 1, wherein the survey is sent to a family member to be completed by the family member.

5. The health management system as set forth in claim 1, wherein the intervention rules include:
    the physiological parameter measurement value being at or beyond a predetermined threshold;
    an answer to the survey matching a preselected criteria;
    the physiological parameter measurement value matching a preselected criteria; and
    the physiological parameter measurement value being beyond a dynamic threshold based on a prior measurements of the physiological parameter.

6. The health management system as set forth in claim 1, further including:
a plurality of goal modules assigned to the user, wherein the care plan manager adds, deletes, modifies, and reorders the audio/visual content sessions of the goal modules.

7. The health management system as set forth in claim 6, wherein the care plan manager one of:
performs changes to the goal modules or content sessions automatically,
contacts a health care plan planner, and
based on a pre determined criteria, one of performs changes to the goal modules or content sessions automatically and contacts a heath care plan planner.

8. The health management system as set forth in claim 7, wherein the contact of the planner includes at least one of:
submitting recommended changes to the planner for pre-approval; and
indicating a condition based on the one input.

9. The health management system as set forth in claim 8, wherein the contact of the planner further includes:
a notification to the planner indicating a priority status for the change.

10. The health management system as set forth in claim 1, further including:
a user interface configured for presenting the audio/visual content sessions; and
a server storing (i) the goal modules, and (ii) at least one user profile indicating at least which goal module or goal modules are assigned to a user profiled by the at least one user profile,
wherein a computer embodies at least the server, the user interface, and an intervention rules engine, and
wherein the at least one patient profile consists of exactly one one user profile.

11. The health management system as set forth in claim 1, further including:
a user interface configured for presenting the audio/visual content sessions; and
a server storing (i) the goal modules, and (ii) at least one one user profile indicating at least which goal module or goal modules are assigned to a one user profiled by the at least one one user profile,
wherein the at least one patient profile includes a plurality of one user profiles, and the server communicates with user interfaces associated with a plurality of different one users, each one user being profiled by a corresponding one user profile.

12. A health management system comprising:
goal modules each including one or more content sessions cooperatively directed toward achieving a projected health management goal;
at least one feedback path providing at least one input indicative of a trend in a patient's progress toward achieving the projected health management goal;
a care plan manager which dynamically configures or modifies at least one of the goal modules and content sessions based at least on the one input and intervention rules so that the patient's progress toward the projected health management goal is optimized;
a user interface configured for presenting the content sessions, wherein the user interface includes a television set on which the content sessions are displayed, and the at least one feedback path includes a television remote; and
a server storing (i) the goal modules, and (ii) at least one patient profile indicating at least which goal module or goal modules are assigned to a patient by the at least one patient profile.

13. A health management system comprising:
a care plan server communicating with a plurality of patients, the care plan server storing at least:
a plurality of content sessions directed toward achieving a health management goal, and
a plurality of patient profiles each corresponding to a respective patient; and
a care plan manager configured to control presentation of the content sessions to each patient based on:
at least one feedback input from the patient and intervention rules, and
the patient achieving each of a plurality of designated mile posts toward achieving the health management goal.

14. The health management system as set forth in claim 13, further including:
an analyzing algorithm which continually analyzes the feedback inputs from individual patients in response to the presentation of the content sessions and wherein, based on the analysis, the care plan manager reconfigures an order of the content sessions directed toward a particular health management goal.

15. The health management system as set forth in claim 13, wherein the content sessions include audio/video presentations designed to motivate each patient to achieve the health management goal.

16. A health management system including:
a host center which includes the care plan server as set forth in claim 13; and
a plurality of patient stations each connected with the host center to generate and provide the at least one feedback causing the care plan manager to select which of a plurality of available content sessions are presented and repeated in accordance with the provided feedback.

17. A health management system comprising:
one or more processors programmed to:
electronically receiving at least one input from a patient indicative of a trend in patient progress toward achieving a health management goal;
automatically electronically configuring or modifying a plurality of content sessions which make up a goal module based on intervention rules;
analyzing the trends from the patient in response to the presentation of the content sessions; and
based on the analysis, reconfiguring the content sessions of the goal module directed toward a particular health management goal to improve achieving the particular health management goal; and
a display on which the content sessions are displayed to the patient.

18. The health management system as set forth in claim 17, wherein the one input is generated by a biometric monitoring device.

19. The health management system as set forth in claim 18, wherein the processor is further programmed to:
generate a survey in response to the trend in the one input; and
send the survey to a display device of a third party.

20. The health management method as set forth in claim 18, wherein the trend includes at least one of:
a physiological parameter measurement value beyond a predetermined threshold;

an answer to the survey which matches a preselected criteria;
a physiological parameter measurement value which matches a preselected criteria;
a physiological parameter measurement value beyond a dynamic threshold based on a prior measurement of the physiological parameter; and
deviation between a measured physiological parameter trend and a target physiological parameter trend.

21. A health management method comprising:
with one or more processors, providing a care plan to a cable or set top box of a patient, wherein said care plan includes one or more goal modules, each containing a plurality of audio/video content sessions which are presented to the patient on an audio/video display device connected with the cable or set top box;
electronically receiving feedback from the patient via the cable or set top box;
with the one or more processors, generating a behavioral model and using the feedback received from the patient as an input to the behavioral model, wherein the behavioral model tracks the patient's progress within one or more of the goal modules;
wherein the behavioral model determines a current stage in each of the goal models to which the patient has progressed;
displaying said audio/video content sessions to the patient on said audio/video display device; and
with the one or more processors, reporting the stages to a display device of a care provider.

22. A health management method comprising:
with one or more processors, providing a care plan to a cable or set top box of a patient, wherein said care plan includes one or more goal modules, each containing a plurality of audio/video content sessions which are presented to the patient on an audio/video display device connected with the cable or set top box;
electronically receiving feedback from the patient via the cable or set top box;
with the one or more processors, generating a behavioral model and using the feedback received from the patient as an input to the behavioral model, wherein the behavioral model tracks the patient's progress within one or more of the goal modules;
displaying said audio/video content sessions to the patient on said audio/video display device; and
with the one or more processors, changing the audio/video content sessions in response to the patient processing from a current stage to another stage.

23. A health management method comprising:
with one or more processors, providing a care plan to a cable or set top box of a patient, wherein said care plan includes one or more goal modules, each containing a plurality of audio/video content sessions which are presented to the patient on an audio/video display device connected with the cable or set top box;
electronically receiving feedback from the patient via the cable or set top box;
with the one or more processors, generating a behavioral model and using the feedback received from the patient as an input to the behavioral model, wherein the behavioral model tracks the patient's progress within one or more of the goal modules;
displaying said audio/video content sessions to the patient on said audio/video display device; and
with the one or more processors, automatically electronically configuring or modifying at least one of goal modules and content sessions based on an output from the behavioral model.

24. A health management method comprising:
with a cable or set top box, providing a patient with a care plan including one or more goal modules, each goal module comprising a plurality of content sessions;
with a processor, interleaving content sessions of the goal modules and forwarding the interleaved content sessions to a user display device;
on the user display device, displaying the content sessions;
with the processor, electronically receiving feedback from the patient;
with the processor, using the feedback received from the patient to assess a stage of one or more goal modules;
with the processor, in response to the received feedback and the assessed states, reordering or replacing at least one of the content sessions forwarded to the patient for display on the display device.

25. The health management method as set forth in claim 24 wherein the stages for each of the goal modules are assessed based on a common stage continuum.

26. The health management system as set forth in claim 24 wherein a behavioral model is used by the processor to access the stage of the one or more goal modules.

27. The health management method as set forth in claim 26 wherein the processor automatically electronically configures or modifies at least one of goal modules and content sessions based on an output from the behavioral model.

28. The health management method as set forth in claim 24 wherein the content sessions include video presentations configured to motivate the patient to a goal of the goal module.

* * * * *